(12) United States Patent
Cooper, IV et al.

(10) Patent No.: US 12,136,477 B2
(45) Date of Patent: Nov. 5, 2024

(54) MULTIDOSE PACKAGING TARGETING SYSTEM

(71) Applicant: Evernorth Strategic Development, Inc., St. Louis, MO (US)

(72) Inventors: John W. Cooper, IV, St. Louis, MO (US); Susan E. Anselmi, Nutley, NJ (US); Robert Monzyk, St. Louis, MO (US); Brady Novak, St. Charles, MO (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 241 days.

(21) Appl. No.: 17/712,811

(22) Filed: Apr. 4, 2022

(65) Prior Publication Data
US 2022/0367025 A1    Nov. 17, 2022

Related U.S. Application Data

(60) Provisional application No. 63/188,512, filed on May 14, 2021.

(51) Int. Cl.
*G16H 20/13*    (2018.01)
*G06N 3/08*    (2023.01)
*G16H 10/60*    (2018.01)
*G16H 80/00*    (2018.01)

(52) U.S. Cl.
CPC ............. *G16H 20/13* (2018.01); *G06N 3/08* (2013.01); *G16H 10/60* (2018.01); *G16H 80/00* (2018.01)

(58) Field of Classification Search
CPC ........ G16H 20/13; G16H 10/60; G16H 80/00; G06N 3/08
See application file for complete search history.

(56) References Cited

U.S. PATENT DOCUMENTS

| | | |
|---|---|---|
| 7,558,380 B2 | 7/2009 | Divenuta |
| 8,478,611 B2 | 7/2013 | Epstein |
| 9,782,327 B2 | 10/2017 | Miceli |
| 9,785,751 B2 | 10/2017 | Muecke |

(Continued)

OTHER PUBLICATIONS

Bardage, et al. "Patients' perspectives on automated multi-dose drug dispensing." J Community Med Health 6.1 (2016): 393.

*Primary Examiner* — Kenneth Bartley
*Assistant Examiner* — David Choi
(74) *Attorney, Agent, or Firm* — Miller Johnson

(57) ABSTRACT

Methods and systems for performing multidose packaging targeting are provided. The methods and systems perform operations comprising: receiving prescription related complexity data associated with a patient, the prescription related complexity data comprising medication regiment information for a plurality of medications and patient specific information, the prescription related complexity data representing complexity for the patient in adhering to the one or more medications; applying a model to the prescription related complexity data to generate a score for at least one medication of the plurality of medications, the score being indicative of a likelihood of converting the patient from a current dispensing process to an alternate dispensing process; and triggering, based on the generated score, a notification associated with converting the patient from the current dispensing process to the alternate dispensing process.

18 Claims, 9 Drawing Sheets

(56) References Cited

U.S. PATENT DOCUMENTS

| | | |
|---|---|---|
| 10,192,034 B2 | 1/2019 | Epstein |
| 10,351,285 B2 | 7/2019 | Sweet |
| 10,709,642 B2 | 7/2020 | Conlon |
| 10,867,278 B2 * | 12/2020 | Gilman .............. G06Q 20/3224 |
| 10,916,340 B2 | 2/2021 | Hawkes |
| 11,049,616 B2 | 6/2021 | Sellars |
| 11,328,825 B1 * | 5/2022 | Yu .......................... G16H 50/20 |
| 2007/0185614 A1 | 8/2007 | Bain |
| 2010/0100391 A1 * | 4/2010 | Daya ..................... G06Q 50/22 |
| | | 715/764 |
| 2012/0179481 A1 * | 7/2012 | Patel ..................... G06Q 30/02 |
| | | 705/2 |
| 2014/0156064 A1 | 6/2014 | Crawford |
| 2014/0330588 A1 | 11/2014 | Epstein |
| 2018/0082039 A1 | 3/2018 | Hesse |
| 2019/0096526 A1 * | 3/2019 | Hirsch ................ G06F 21/6245 |
| 2019/0156955 A1 * | 5/2019 | Winlo .................... G16H 15/00 |
| 2020/0245925 A1 * | 8/2020 | Inwald .................. G16H 30/20 |

* cited by examiner

CONVERSION NOTIFICATION

The below patient is very likely to convert from current dispensing method to an alternate dispensing method 420 — Select Alternate Dispensing method:

[Multiple-Dose Package] [Other]

410 — Medications Eligible for Conversion:
Medication A
Medication B
Medication C

SELECT TO TRIGGER OUTREACH EVENT

*FIG. 4*

CONVERSION NOTIFICATION

Would you like to convert from your current dispensing method to a multiple-dose package method?

510 — Medications Eligible for Conversion:
Medication A
Medication B
Medication C

SELECT TO CONVERT

*FIG. 5*

MULTIDOSE PACKAGING TARGETING SYSTEM

CROSS-REFERENCE TO RELATED APPLICATION

This application claims the benefit of priority under 35 USC 119(e) of U.S. Provisional Patent Application No. 63/188,512, filed May 14, 2021, the contents of which are incorporated herein by reference in their entirety.

BACKGROUND

Certain patients are placed on medication regiments with a very high medication burden. Specifically, such patients may need to take different medications multiple times throughout the day which makes adhering to the medication regiments increasingly difficult. Pharmacy benefit managers are always seeking new ways to increase medication adherence for such circumstances.

BRIEF DESCRIPTION OF THE DRAWINGS

FIGS. 4 and 5 are example user interfaces of the medication dispensing conversion system, according to example embodiments.

DETAILED DESCRIPTION

Figure 1:
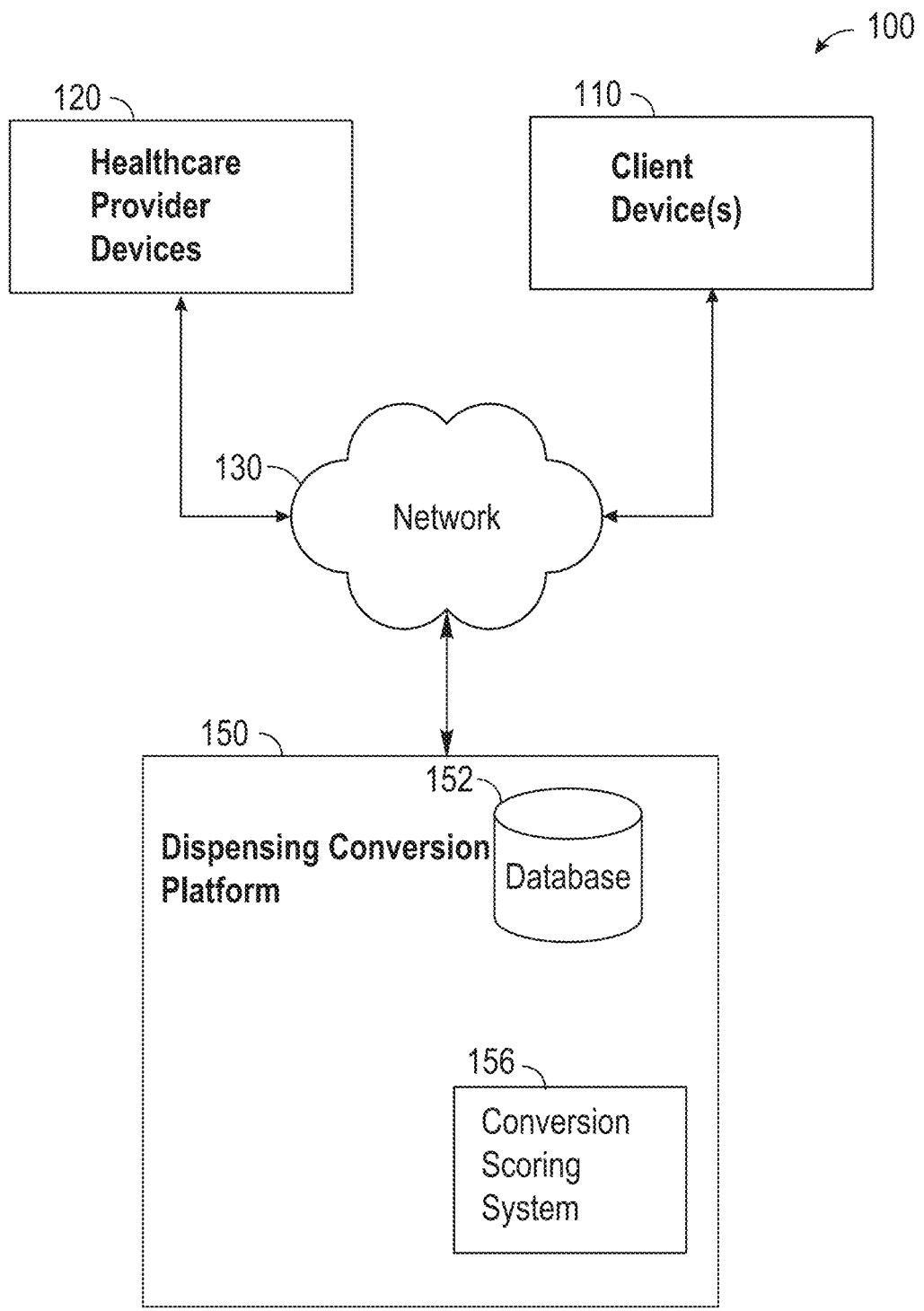
FIG. 1 is a block diagram of an example medication dispensing conversion system, according to some embodiments.

Example methods and systems for a medication dispensing conversion system are provided. In the following description, for purposes of explanation, numerous specific details are set forth in order to provide a thorough understanding of example embodiments. It will be evident, however, to one of ordinary skill in the art that embodiments of the invention may be practiced without these specific details.

Multiple-dose packages or pouches are designed to take the confusion out of medication complexity while increasing medication adherence. Multiple-dose packages include pouches that are organized by the prescribed day and time of the dose and are ideal for patients taking multiple medications, multiple times throughout the day, also called a "high medication burden". Certain medications though may not be compatible with multiple-dose packages. Also, the likelihood of converting certain patients from one dispensing method to a multiple-dose package dispensing method may be low, for example because of the demographics of the patients or the means by which the patients obtain their medications. Finding the right patients and the right medications to suggest for conversion from one dispensing method to a multiple-dose dispensing method can be a very tedious, time consuming and manual process. This causes missed opportunities for reaching patients to convert from one dispensing method to another and results in continued poor adherence of the medications for such patients.

The disclosed embodiments provide systems and methods to automatically detect at-risk patients who may benefit from converting their prescription medication regimens from traditional bottle dispensing to multiple-dose pouch packaging. The disclosed system can analyze prescription claims data and prospectively identify whether a given patient may benefit from an alternate dispensing process, such as multiple-dose packages or a physical mail reminder. The disclosed system can also identify which medications are not compatible for the alternate dispensing process and provide recommendations for other adherence solutions (such as sending reminders by physical mail in the post office or other courier). Prescription Benefit Managers (PBMs) can leverage the disclosed system to advise plan sponsors of opportunities to deploy alternate dispensing processes, such as multiple-dose pouch packaging, to patients where it may provide measurable improvements to medication adherence and ultimately, help plans save money in downstream medical costs. The health plan can leverage the results of application of the model to identify and select groups of patients to associate with a particular or alternative dispensing process. Pharmacies can use the disclosed system to provide adherence counseling to patients and provide the rationale for the method in which each of their medications will be dispensed and optimize downstream fulfillment workflow.

According to some embodiments, prescription related complexity data associated with a patient is received. The prescription related complexity data includes medication regiment information for a plurality of medications and patient specific information, the prescription related complexity data representing complexity for the patient in adhering to the medications. The disclosed embodiments apply a model to the prescription related complexity data to generate a score for at least one medication of the plurality of medications. The score may be indicative of a likelihood of successfully converting the patient from a current dispensing process to an alternate dispensing process. The disclosed embodiments trigger, based on the generated score, a notification associated with converting the patient from the current dispensing process to the alternate dispensing process. In one example, the model includes a machine learning technique that includes a neural network. The machine learning technique is trained to establish a relationship between a plurality of training patient-drug combination features and medication dispensing process conversion likelihoods.

In this way, the disclosed embodiments improve the overall process of medication adherence and specifically improve the efficiency at which patients are identified for conversion from one dispensing method to another. Namely, the disclosed embodiments improve the efficiency and reduce the amount of resources consumed for identifying which medications and which patients are good candidates for recommending conversion from one dispensing method to another dispensing method. In some examples, the model can assist a group of patients (e.g., elderly patients) adhere to their medication regiments by applying the model to suggest an alternate dispensing method or adherence method for such patients. In some cases, a caregiver can be identified or can receive the notification (e.g., a physical mailer relating to medication adherence) and can, in response, elect a specified dispensing method (e.g., a multi-dose packaging dispensing method) for the associated patient under care of the caregiver. The notification, provided by way of the physical mailer, can include a printout or other physical representation (e.g., textual instructions) of the results of applying the model for recommending conversion from one dispensing method to another.

FIG. 1 is a block diagram showing an example medication dispensing conversion system 100 according to various exemplary embodiments. The medication dispensing conversion system 100 includes one or more client devices 110, one or more healthcare provider devices 120, and a medication dispensing conversion platform 150 that are communicatively coupled over a network 130 (e.g., Internet, telephony network).

As used herein, the term "client device" may refer to any machine that interfaces to a communications network (such as network 130) to access the medication dispensing conversion platform 150. The client device 110 may be, but is not limited to, a mobile phone, desktop computer, laptop, portable digital assistants (PDAs), smart phones, a wearable device (e.g., a smart watch), tablets, ultrabooks, netbooks, laptops, multi-processor systems, microprocessor-based or programmable consumer electronics, game consoles, set-top boxes, or any other communication device that a user may use to access a network or the medication dispensing conversion platform 150.

In some cases, the medication dispensing conversion platform 150 is accessible over a global communication system, e.g., the Internet or world wide web. In such instances, the medication dispensing conversion platform 150 hosts a website that is accessible to the client devices 110. Upon accessing the website, the client devices 110 provide secure login credentials, which are used to access a profile associated with the login credentials. One or more user interfaces associated with the medication dispensing conversion platform 150 are provided over the Internet via the website to the client devices 110.

Healthcare provider devices 120 can include the same or similar functionality as client devices 110 for accessing the medication dispensing conversion platform 150. In some cases, the healthcare provider devices 120 are used by "internal" users. Internal users are personnel, such as physicians, clinicians, healthcare providers, health-related coaches PBM operators, pharmacists, or the like that are associated with or employed by an organization that provides the medication dispensing conversion platform 150. In some cases, the healthcare provider devices 120 are used by "external" users. External users are personnel, such as physicians, clinicians, and health-related coaches that are associated with or employed by a different (external) organization than that which provides the medication dispensing conversion platform 150.

The healthcare provider devices 120, when used by internal or external users, to access the medication dispensing conversion platform 150 can view many records associated with many different patients (or users associated with client devices 110). Different levels of authorization can be associated with different internal and different external users to control which records the internal and external users have access. In some instances, only records associated with those patients to which a given internal or external user is referred (e.g., as a result of a conversion recommendation made by the conversion scoring system 156 for a given user or patient), are made accessible and available to the given internal or external user device. Sometimes, a first internal or external user can refer a patient or records associated with the patient to a second internal or external user. In such circumstances, the second internal or external user becomes automatically authorized to access and view the patient's records that were referred by the first internal or external user. In an example embodiment, an outreach event or flag can be set in a patient record in the database at the medication dispensing conversion platform 150 in response to the conversion scoring system 156 predicting or generating a high score (score that exceeds a threshold value) for one or more medications associated with a given patient. The referral event or flag provides authorization to a user of the healthcare provider devices 120 to view patient records and contact the patient (e.g., to discuss a possible conversion from a current dispensing method or process to an alternate dispensing method or process).

The network 130 may include, or operate in conjunction with, an ad hoc network, an intranet, an extranet, a virtual private network (VPN), a local area network (LAN), a wireless network, a low energy Bluetooth (BLE) connection, a WiFi direct connection, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The healthcare provider devices 120 can be used to access pharmacy claims, medical data (e.g., medical information 230 stored in database 152), laboratory data and the like for one or more patients that the healthcare provider devices 120 are authorized to view. This patient information 210 can be maintained in a database 152 by the medication dispensing conversion platform 150 or in a third-party database accessible to the medication dispensing conversion platform 150 and/or the healthcare provider devices 120.

In some embodiments, the client devices 110 and the medication dispensing conversion platform 150 can be communicatively coupled via an audio call (e.g., VoIP, Public Switched Telephone Network, cellular communication network, etc.) or via electronic messages (e.g., online chat, instant messaging, text messaging, email, and the like). While FIG. 1 illustrates a single client device 110 and a single healthcare provider device 120, it is understood that a plurality of such devices can be included in the system 100 in other embodiments. As used herein, the term "client device" may refer to any machine that interfaces to a communications network (such as network 130) to obtain resources from one or more server systems or other client devices.

The medication dispensing conversion platform 150 can be a human agent or an automated agent, e.g., on behalf of an organization. The automated agent can be associated with a medical group that includes the member. The automated agent can be an interactive voice response (IVR), a virtual online assistant, or a chatbot provided on a website. During a communication session between the user and the agent, the medication dispensing conversion platform 150 identifies the member using initial context data (e.g., the phone number the member is calling from, the website login information inputted, automatic number identification (ANI), etc.) and retrieves the data on the member (e.g., member account information, name, address, insurance information, information on spouse and dependents, etc.) to be presented on the client device 110.

In some embodiments, the medication dispensing conversion platform 150 includes a conversion scoring system 156. As explained in more detail in connection with FIG. 3, the conversion scoring system 156 is trained based on training patient-drug combinations and their corresponding ground-truth medication dispensing process conversion likelihoods. The conversion scoring system 156 is trained to predict a likelihood of conversion score for each medication associated with a given patient based on features of a given patient-drug combination. For example, the conversion scoring system 156 generates a prediction or set of likelihoods of each medication associated with the given patient. The prediction or set of likelihoods each indicate a likelihood that the given patient will successfully convert from their current dispensing method to another dispensing method, such as from having each of a plurality of medications dispensed individually to dispensing two or more of the plurality of medications in a multiple-dose package.

In some embodiments, the conversion scoring system 156 is trained by obtaining a batch of training data comprising a first set of the plurality of training patient-drug combination features and medication dispensing process conversion likelihood and processing the first set of the plurality of training patient-drug combination features with the machine learning technique to generate an estimated medication dispensing process conversion likelihood. The conversion scoring system 156 computes a loss based on a deviation between the estimated medication dispensing process conversion likelihood and the corresponding medication dispensing process conversion likelihood of the first set of the plurality of training patient-drug combination features. Parameters of the conversion scoring system 156 are updated based on the computed deviation. After processing a certain quantity or batch of training data or when a stopping criterion is met, the machine learning model implemented by the conversion scoring system 156 is output as a trained machine learning model that can generate a score for new patient-drug combination features. In some examples, the training data is updated on a periodic or real-time basis based on a result or outcome of delivering a particular notification to a patient. In such instances, the model is retrained based on the updated training data to refine future score generations.

The score is used to trigger a notification associated with converting the patient from the current dispensing process to the alternate dispensing process. For example, a message can be provided to an operator of a PBM in which the message identifies the patient and the score associated with at least one medication of a plurality of medications. The operator can then perform an outreach event to communicate with the patient to modify the current dispensing process. As another example, a message can be provided to the patient with an option to automatically modify the current dispensing process to an alternate dispensing process, such as a multiple-dose package.

Figure 2:
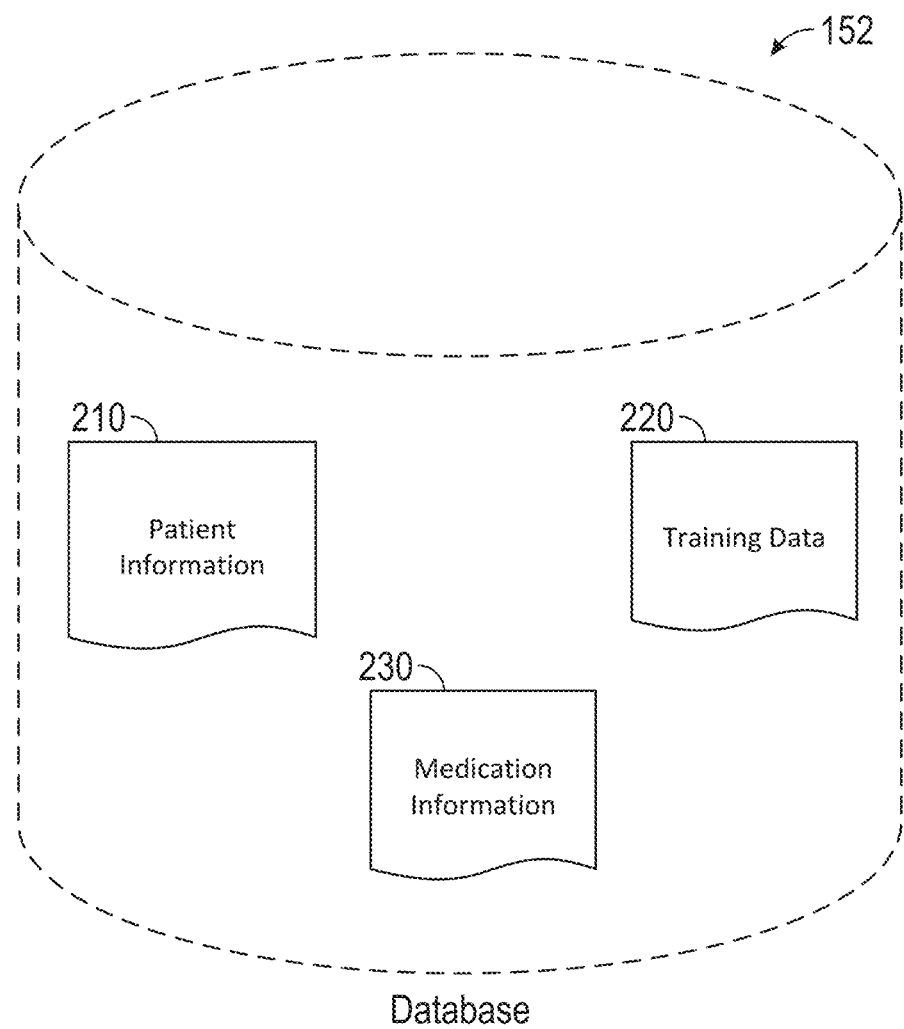
FIG. 2 is an example database that may be deployed within the system of FIG. 1, according to some embodiments.

FIG. 2 is an example database 152 that may be deployed within the system of FIG. 1, according to some embodiments. The database 152 includes patient information 210, medication information 230, and training data 220. The patient information 210 can be generated by the dispensing conversion platform 150. For example, after the dispensing conversion platform 150 can access one or more patient records from one or more sources, including pharmacy claims, benefit information, prescribing physician information, dispensing information (e.g., where and how the patient obtains their current medications), demographic information, and so forth. The dispensing conversion platform 150 can collect this information from the patient records and generates a patient features vector that includes this information.

The medication information 230 stores various medication related information (e.g., prescriptions, size of the medication or pills, compatible forms of dispensing information, temperature control information, mixing exclusion information, and so forth) for various medications. The size of the medication or pills may be used to determine whether such medication can be dispensed using an alternate dispensing method, such as through a multiple-dose package. The compatible forms of dispensing information can indicate or list the way in which the medication can be dispensed, such as through typical pill bottle, multiple-dose packages, specialty pharmacy, home delivery, and so forth. The mixing exclusion information indicates a list of medications that cannot touch or be in close proximity to a given medication. This information can be used to avoid combining two medications in the same multiple-dose package where the two medications are not allowed to be in close proximity to each other. Such medication information 230 is used by the medication dispensing conversion platform 150 to adjusts or assign weights to scores indicating likelihood of conversion of different medications and to determine whether or not different medications are suitable or compatible with suggesting for alternate dispensing methods.

The training data 220 includes training patient-drug combination features and medication dispensing process conversion likelihood. The training data 220 is used to train a machine learning model implemented by the conversion scoring system 156 to generate scores indicating likelihoods of conversion from one dispensing method to another. For example, the training data 220 can be built over time by identifying a set of patients who were successfully converted from one dispensing method to another (e.g., patients who agreed to convert their current dispensing method to another) and including the medications associated with such patients. As another example, a first set of the training data 220 can be used to initially train the model. Then, the training data 220 can be updated based on information received from a target entity representing a set of patients who were successfully converted from one dispensing method to another (e.g., patients who agreed to convert their current dispensing method to another) and including the medications associated with such patients. The updated training data 220 can be used to re-train the model to refine results generated by the re-trained model.

Patient and medication information for these patients is collected and used to generate patient-drug combination features. Another set of patients can also be identified who were unsuccessfully converted from one dispensing method to another (e.g., patients who did not agree to convert their current dispensing method to another or who were not recommended for conversion) and including the medications associated with such patients. Patient and medication information for these other set of patients is collected and used to generate patient-drug combination features. In this way, the training patient-drug combination features includes information on patients who were successfully converted and patients who were unsuccessfully converted from one dispensing method to another on an individual or combination of drugs basis. The information about successful and unsuccessful conversions can be collected by the same entity that runs the model and trains/re-trains the model. In some other examples, the information about successful and unsuccessful conversions can be collected by a second server associated with a target entity to which results of applying the model are delivered and the information is used by a first server to run and retrain the model on a continuous basis or periodic basis.

In one example, to generate the training data 220 a set of rules can be applied to a collection of patients and their medications. The set of rules can be used to filter out or identify patients to recommend for conversion. For example, the set of rules can consider various criteria in identifying the patients and medications. Such criteria can include any combination of profitability information indicative of a level of profitability from converting the patient from the current dispensing process to the alternate dispensing process, quantity of pharmacies used to obtain the plurality of medications, quantity of prescribing physicians of the plurality of medications, history of adherence to the plurality of medications, and/or patient demographic information.

Once such patients are identified, the patients are contacted to convert from their current dispensing method to an alternate dispensing method. If the patients agree to the conversion, the training data 220 is updated to indicate a successful conversion for the particular patients and medications. If the patients do not agree to the conversion, the training data 220 is updated to indicate an unsuccessful conversion for the particular patients and medications. After a specified quantity of patients and medications are processed, the training patient-drug combination features are generated and stored in the training data 220 and used to train the machine learning model of the conversion scoring system 156.

Figure 3:
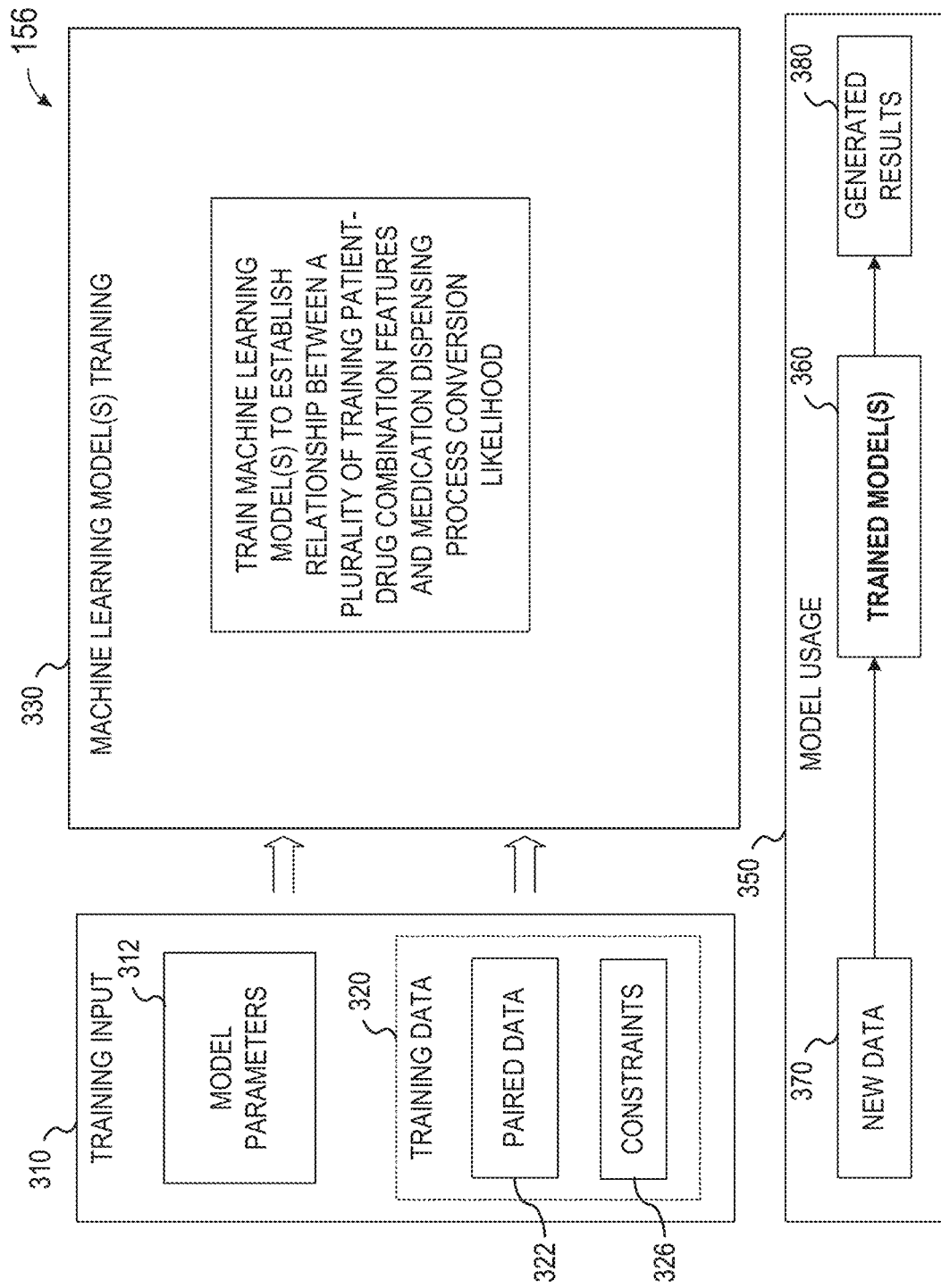
FIG. 3 is a block diagram of an example conversion scoring system that may be deployed within the system of FIG. 1, according to some embodiments.

FIG. 3 is a block diagram of an example conversion scoring system 156 that may be deployed within the system of FIG. 1, according to some embodiments. Training input 310 includes model parameters 312 and training data 320 (e.g., training data 220 (FIG. 2)) which may include paired training data sets 322 (e.g., input-output training pairs) and constraints 326. Model parameters 312 stores or provides the parameters or coefficients of corresponding ones of machine learning models. During training, these parameters 312 are adapted based on the input-output training pairs of the training data sets 322. After the parameters 312 are adapted (after training), the parameters are used by trained models 360 to implement the trained machine learning models on a new set of data 370.

Training data 320 includes constraints 326 which may define the constraints of a given medication or collection of medications, such as the types of dispensing methods compatible with the medications and restrictions associated with such medications (e.g., whether or not the medications can be mixed together or stored together with other medications and temperature control restrictions for the medications). The paired training data sets 322 may include sets of input-output pairs, such as a pairs of a plurality of training patient-drug combination features and medication dispensing process conversion likelihoods. Some components of training input 310 may be stored separately at a different off-site facility or facilities than other components.

Machine learning model(s) training 330 trains one or more machine learning techniques based on the sets of input-output pairs of paired training data sets 322. For example, the model training 330 may train the machine learning (ML) model parameters 312 by minimizing a loss function based on one or more ground-truth medication dispensing process conversion likelihoods (e.g., indicating whether a patient with the given set of patient-drug combination features was successfully converted from one dispensing method to another). The ML model can include any one or combination of classifiers or neural networks, such as an artificial neural network, a convolutional neural network, an adversarial network, a generative adversarial network, a deep feed forward network, a radial basis network, a recurrent neural network, a long/short term memory network, a gated recurrent unit, an auto encoder, a variational autoencoder, a denoising autoencoder, a sparse autoencoder, a Markov chain, a Hopfield network, a Boltzmann machine, a restricted Boltzmann machine, a deep belief network, a deep convolutional network, a deconvolutional network, a deep convolutional inverse graphics network, a liquid state machine, an extreme learning machine, an echo state network, a deep residual network, a Kohonen network, a support vector machine, a neural Turing machine, and the like.

Particularly, the ML model can be applied to a training plurality of training patient-drug combination features to estimate or generate a prediction with a certain level of likelihood or probability of medication dispensing process conversion likelihoods. In some implementations, a derivative of a loss function is computed based on a comparison of the estimated medication dispensing process conversion likelihoods (the likelihood or probability of the patient-drug combination being successfully converted) and the ground truth medication dispensing process conversion likelihoods associated with the training patient-drug combination and parameters of the ML model are updated based on the computed derivative of the loss function.

In one example, the ML model receives a batch of training data that includes a first set of the plurality of training patient-drug combination features together with medication dispensing process conversion likelihoods (e.g., whether the medications associated with each training patient resulted in a successful conversion from one dispensing method to another). The ML model generates a feature vector based on the first set of the plurality of training patient-drug combination features and generates a prediction of conversion likelihood on the feature vector. The prediction is compared with the ground truth indication of whether the patient was successfully converted and parameters of the ML model are updated based on the comparison.

The result of minimizing the loss function for multiple sets of training data trains, adapts, or optimizes the model parameters 312 of the corresponding ML models. In this way, the ML model is trained to establish a relationship between a plurality of training patient-drug combination features and medication dispensing process conversion likelihoods.

The ML model is trained in one implementation according to supervised learning techniques to estimate medication dispensing process conversion likelihoods for patient-drug combination features. In such cases, to train the ML model, a plurality of patient-drug combination features are retrieved together with their corresponding training medication dispensing process conversion likelihoods. The ML model is applied to a first batch of training patient-drug combination features to estimate likelihoods of conversions for each medication associated with the patient-drug combination features. The batch of the training patient-drug combination features can be used to train the ML model with the same parameters of the ML model and may range from one training patient-drug combination feature to all of the training patient-drug combination features. The estimated or predicted likelihoods are compared with the ground-truth medication dispensing process conversion likelihoods corresponding to the training patient-drug combination feature to compute a loss based on a loss function and a gradient or derivative of the loss function with the applied losses is computed. Based on the gradient or derivative of the loss function, updated parameters for the ML model are computed. The ML model is then applied with the updated parameters to a second batch of training patient-drug combination feature to again estimate a given set of likelihoods and apply the likelihoods predictions to a loss function to compute loss based on the ground-truth likelihoods of conversion associated with the training patient-drug combination feature. Parameters of the ML model are again updated and iterations of this training process continue for a specified number of iterations or epochs or until a given convergence criteria has been met.

After the machine learning model is trained, new data 370, including one or more patient-drug combination features are received (e.g., list of medications associated with the patient, demographics of the patient, adherence information for the patient, dispensing methods associated with the medications, and number of prescribing physicians of the medications), may be received. The trained machine learning technique may be applied to the new data 370 to generate results 380 including a prediction of a plurality of scores for each of the plurality of medications each being indicative of a likelihood that the patient will be converted from the current dispensing method to an alternate dispensing method.

The scores are used to trigger a notification associated with converting the patient from the current dispensing process to the alternate dispensing process. For example, as shown in FIG. 4, a message 400 can be provided to an operator of a PBM on a healthcare provider device 120. The message 400 identifies the patient and the score associated with at least one medication of a plurality of medications. The message can list the medications eligible for conversion according to their scores. Namely, the medications can be sorted or ranked based on the scores and displayed in region 410. The healthcare provider device 120 can receive a user selection of an option displayed in region 410 to trigger an outreach event. The outreach event identifies the list of medications and establishes contact with the patient to convert the patient from obtaining the medications using the current dispensing method or process to an alternate dispensing method or process, such as by combining the medications listed in region 410 into a multiple-dose package. The healthcare provider device 120 can receive input from the operator of the alternate dispensing method from region 420. For example, the operator can select a multiple-dose package option to suggest to the patient to combine the medications into the multiple-dose package. In response to determining that one or more of the medications is not eligible for the multiple-dose package, an alternate dispensing method can be suggested. For example, the alternate dispensing method can include any one or more of: providing automatic dose and refill reminders, providing automatic refill and renewal for the plurality of medications, synchronizing medication, identifying lower cost alternatives, providing home delivery of the plurality of medications, and providing one or more adherence aids. The operator can then perform an outreach event to communicate with the patient to modify the current dispensing process.

As another example, a message can be provided to the patient with an option to automatically modify the current dispensing process to an alternate dispensing process, such as a multiple-dose package. For example, as shown in FIG. 5, a message 500 can be provided to an patient of on a client device 110. The message 500 identifies the patient and indicates that the patient has one or more medications that are eligible for an alternative dispensing method, such as a multiple-dose package dispensing method. The message 500 can list the medications eligible for conversion according to their scores. Namely, the medications can be sorted or ranked based on the scores and displayed in region 510. The client device 110 can receive a user selection of an option displayed in region 510 to convert the current dispensing method to the alternative dispensing method that is indicated in the message 500. In response, the PBM is informed by sending a message from the client device 110 indicating confirmation of the conversion for the patient. The next dosage of the medication is then provided to the patient via the alternative dispensing method. Also, the training data 220 is updated with the combination of patient-drug features of this patient and an indication of a successful conversion.

Figure 6:
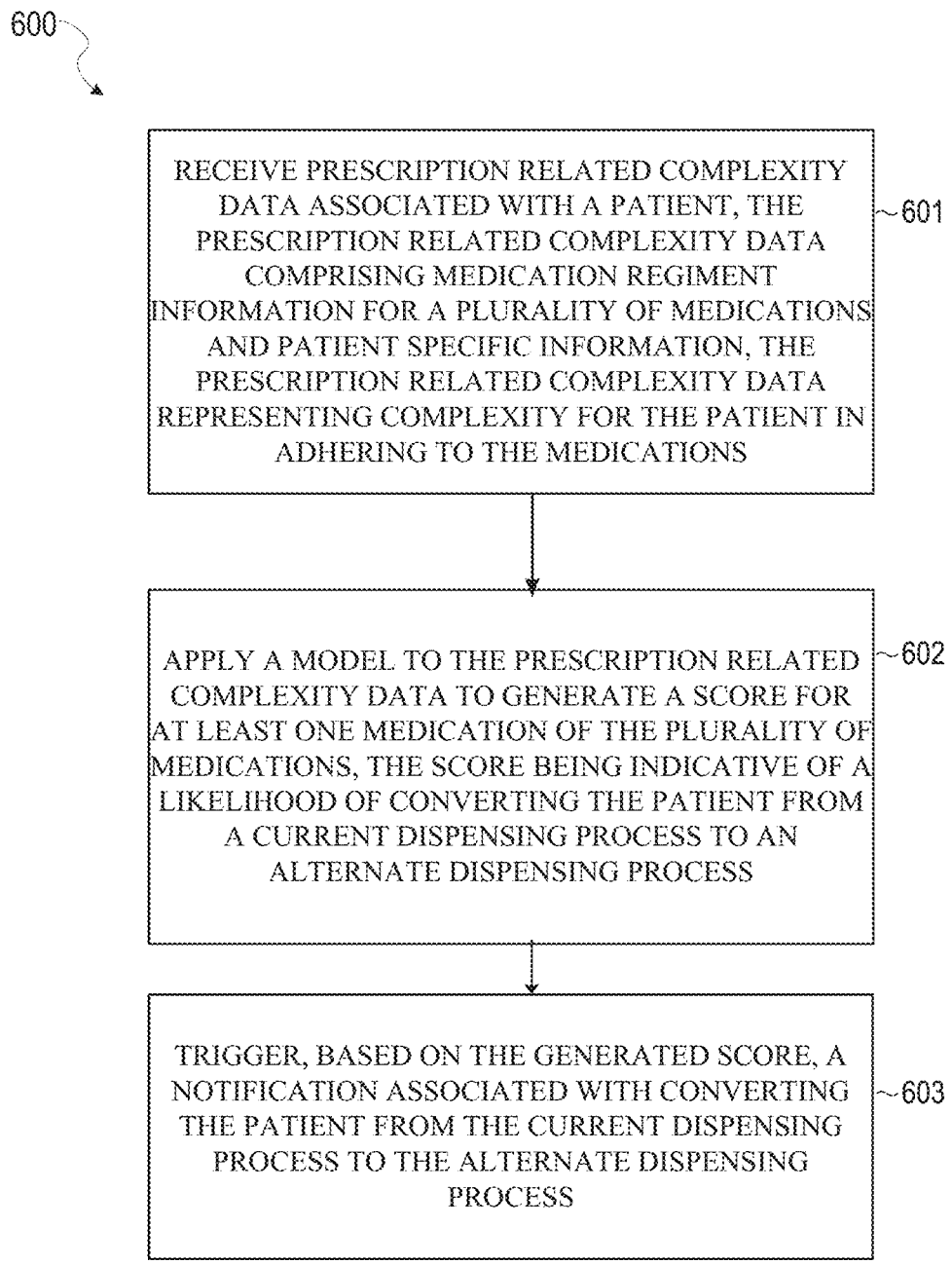
FIG. 6 is a flowchart illustrating example operations of the medication dispensing conversion system, according to example embodiments.

FIG. 6 is a flowchart illustrating example operations of the medication dispensing conversion system in performing process 600, according to example embodiments. The process 600 may be embodied in computer-readable instructions for execution by one or more processors such that the operations of the process 600 may be performed in part or in whole by the functional components of the system 100; accordingly, the process 600 is described below by way of example with reference thereto. However, in other embodiments, at least some of the operations of the process 600 may be deployed on various other hardware configurations. Some or all of the operations of process 600 can be in parallel, out of order, or entirely omitted.

At operation 601, the system 100 receives prescription related complexity data associated with a patient, the prescription related complexity data comprising medication regiment information for a plurality of medications and patient specific information, the prescription related complexity data representing complexity for the patient in adhering to the plurality of medications.

At operation 602, the system 100 applies a model to the prescription related complexity data to generate a score for at least one medication of the plurality of medications, the score being indicative of a likelihood of converting the patient from a current dispensing process to an alternate dispensing process.

At operation 603, the system 100 triggers, based on the generated score, a notification associated with converting the patient from the current dispensing process to the alternate dispensing process. For example, the notification can be provided to a PBM, health plan manager, pharmacy, physician, caregiver, and/or any combination thereof to select one or more associated patients or medication regiments for an alternate dispensing methods or for a particular adherence method. As another example, the alternate dispensing process or adherence protocol or reminder associated with a result of application of the model (e.g., the generated score) can be communicated by the notification electronically (e.g., by email) or by physical medium, such as a mailer delivered by a postal service to a patient or caregiver.

In some cases, the model can be run by a server associated with a first entity (e.g., a PBM) and the results of application of the model can be delivered to a server associated with a second entity (e.g., a pharmacy, health plan administrator, physician, or other entity). In some cases, the model can be run by a server associated with a particular entity to generate the results (e.g., the score) and the particular entity can communicate the results directly to a patient, physician, pharmacist, or other operator. In some examples, the first entity and the second entity can establish a relationship so the first entity applies the model and generates results using a first server and the results or outcome associated with converting a patient from one dispensing process to another are returned from the server associated with a second server back to first server to be used as training data to re-train the model using the first server.

Figure 7:
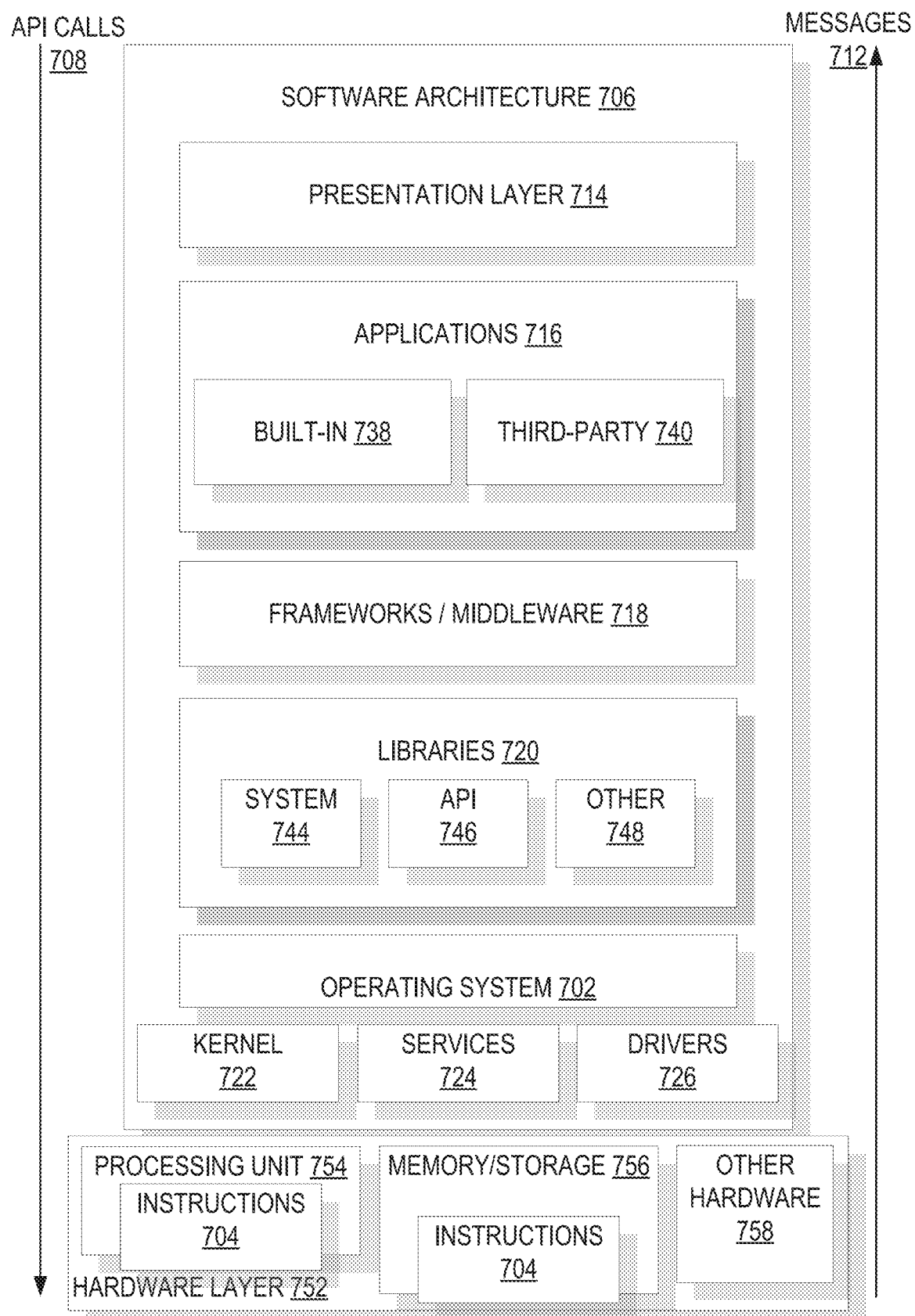
FIG. 7 is a block diagram illustrating an example software architecture, which may be used in conjunction with various hardware architectures herein described.

FIG. 7 is a block diagram illustrating an example software architecture 706, which may be used in conjunction with various hardware architectures herein described. FIG. 7 is a non-limiting example of a software architecture and it will be appreciated that many other architectures may be implemented to facilitate the functionality described herein. The software architecture 706 may execute on hardware such as machine 800 of FIG. 8 that includes, among other things, processors 804, memory 814, and input/output (I/O) components 818. A representative hardware layer 752 is illustrated and can represent, for example, the machine 800 of FIG. 8. The representative hardware layer 752 includes a processing unit 754 having associated executable instructions 704. Executable instructions 704 represent the executable instructions of the software architecture 706, including implementation of the methods, components, and so forth described herein. The hardware layer 752 also includes memory and/or storage devices memory/storage 756, which also have executable instructions 704. The hardware layer 752 may also comprise other hardware 758. The software architecture 706 may be deployed in any one or more of the components shown in FIG. 1. The software architecture 706 can be utilized to apply a machine learning technique or model to generate a prediction of a plurality of scores for each of the plurality of medications for a patient each being indicative of a likelihood that the patient will be converted from the current dispensing method to an alternate dispensing method.

In the example architecture of FIG. 7, the software architecture 706 may be conceptualized as a stack of layers where each layer provides particular functionality. For example, the software architecture 706 may include layers such as an operating system 702, libraries 720, frameworks/middleware 718, applications 716, and a presentation layer 714. Operationally, the applications 716 and/or other components within the layers may invoke API calls 708 through the software stack and receive messages 712 in response to the API calls 708. The layers illustrated are representative in nature and not all software architectures have all layers. For example, some mobile or special purpose operating systems may not provide a frameworks/middleware 718, while others may provide such a layer. Other software architectures may include additional or different layers.

The operating system 702 may manage hardware resources and provide common services. The operating system 702 may include, for example, a kernel 722, services 724, and drivers 726. The kernel 722 may act as an abstraction layer between the hardware and the other software layers. For example, the kernel 722 may be responsible for memory management, processor management (e.g., scheduling), component management, networking, security settings, and so on. The services 724 may provide other common services for the other software layers. The drivers 726 are responsible for controlling or interfacing with the underlying hardware. For instance, the drivers 726 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 720 provide a common infrastructure that is used by the applications 716 and/or other components and/or layers. The libraries 720 provide functionality that allows other software components to perform tasks in an easier fashion than to interface directly with the underlying operating system 702 functionality (e.g., kernel 722, services 724 and/or drivers 726). The libraries 720 may include system libraries 744 (e.g., C standard library) that may provide functions such as memory allocation functions, string manipulation functions, mathematical functions, and the like. In addition, the libraries 720 may include API libraries 746 such as media libraries (e.g., libraries to support presentation and manipulation of various media format such as MPREG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 720 may also include a wide variety of other libraries 748 to provide many other APIs to the applications 716 and other software components/devices.

The frameworks/middleware 718 (also sometimes referred to as middleware) provide a higher-level common infrastructure that may be used by the applications 716 and/or other software components/devices. For example, the frameworks/middleware 718 may provide various graphic user interface functions, high-level resource management, high-level location services, and so forth. The frameworks/middleware 718 may provide a broad spectrum of other APIs that may be utilized by the applications 716 and/or other software components/devices, some of which may be specific to a particular operating system 702 or platform.

The applications 716 include built-in applications 738 and/or third-party applications 740. Examples of representative built-in applications 738 may include, but are not limited to, a contacts application, a browser application, a book reader application, a location application, a media application, a messaging application, and/or a game application. Third-party applications 740 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 740 may invoke the API calls 708 provided by the mobile operating system (such as operating system 702) to facilitate functionality described herein.

The applications 716 may use built-in operating system functions (e.g., kernel 722, services 724, and/or drivers 726), libraries 720, and frameworks/middleware 718 to create UIs to interact with users of the system. Alternatively, or additionally, in some systems, interactions with a user may occur through a presentation layer, such as presentation layer 714. In these systems, the application/component "logic" can be separated from the aspects of the application/component that interact with a user.

Figure 8:
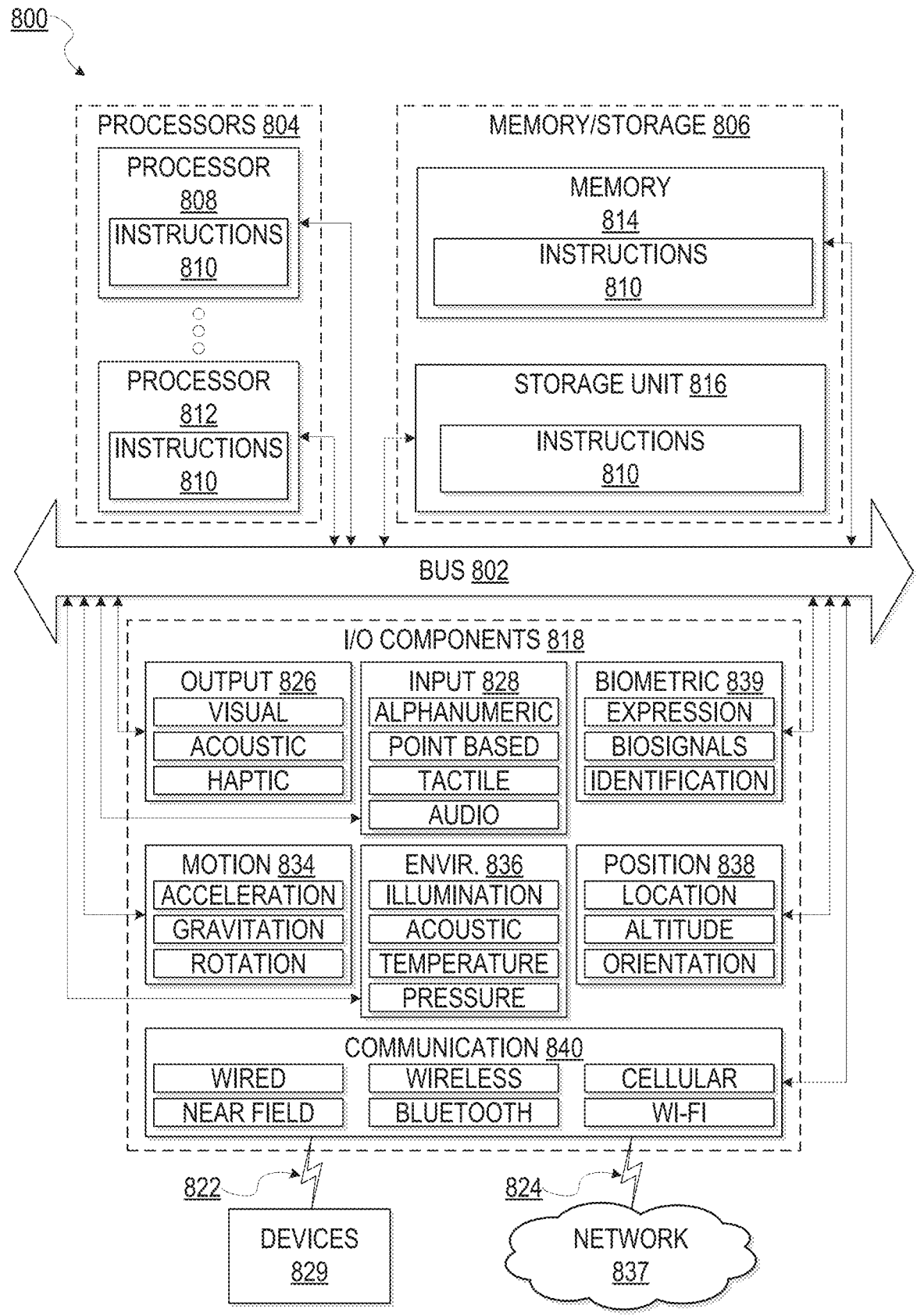
FIG. 8 is a block diagram illustrating components of a machine, according to some example embodiments.

FIG. 8 is a block diagram illustrating components of a machine 800, according to some example embodiments, able to read instructions from a machine-readable medium (e.g., a machine-readable storage medium) and perform any one or more of the methodologies discussed herein. Specifically, FIG. 8 shows a diagrammatic representation of the machine 800 in the example form of a computer system, within which instructions 810 (e.g., software, a program, an application, an applet, an app, or other executable code) for causing the machine 800 to perform any one or more of the methodologies discussed herein may be executed. For example, the instructions 810 may be executed by the system 100 to process a combination of patient-drug features with a trained machine learning model to predict a plurality of scores for each of the plurality of medications each being indicative of a likelihood that the patient will be converted from the current dispensing method to an alternate dispensing method.

As such, the instructions 810 may be used to implement devices or components described herein. The instructions 810 transform the general, non-programmed machine 800 into a particular machine 800 programmed to carry out the described and illustrated functions in the manner described. In alternative embodiments, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to a server computer, a client computer, a personal computer (PC), a tablet computer, a laptop computer, a netbook, a STB, a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 810, sequentially or otherwise, that specify actions to be taken by machine 800. Further, while only a single machine 800 is illustrated, the term "machine" shall also be taken to include a collection of machines that individually or jointly execute the instructions 810 to perform any one or more of the methodologies discussed herein.

The machine 800 may include processors 804, memory/storage 806, and I/O components 818, which may be configured to communicate with each other such as via a bus 802. In an example embodiment, the processors 804 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 808 and a processor 812 that may execute the instructions 810. The term "processor" is intended to include multi-core processors 804 that may comprise two or more independent processors (sometimes referred to as "cores") that may execute instructions contemporaneously. Although FIG. 8 shows multiple processors 804, the machine 800 may include a single processor with a single core, a single processor with multiple cores (e.g., a multi-core processor), multiple processors with a single core, multiple processors with multiple cores, or any combination thereof.

The memory/storage 806 may include a memory 814, such as a main memory, or other memory storage, database 152, and a storage unit 816, both accessible to the processors 804 such as via the bus 802. The storage unit 816 and memory 814 store the instructions 810 embodying any one or more of the methodologies or functions described herein. The instructions 810 may also reside, completely or partially, within the memory 814, within the storage unit 816, within at least one of the processors 804 (e.g., within the processor's cache memory), or any suitable combination thereof, during execution thereof by the machine 800. Accordingly, the memory 814, the storage unit 816, and the memory of processors 804 are examples of machine-readable media.

The I/O components 818 may include a wide variety of components to receive input, provide output, produce output, transmit information, exchange information, capture measurements, and so on. The specific I/O components 818 that are included in a particular machine 800 will depend on the type of machine. For example, portable machines such as mobile phones will likely include a touch input device or other such input mechanisms, while a headless server machine will likely not include such a touch input device. It will be appreciated that the I/O components 818 may include many other components that are not shown in FIG. 8. The I/O components 818 are grouped according to functionality merely for simplifying the following discussion and the grouping is in no way limiting. In various example embodiments, the I/O components 818 may include output components 826 and input components 828. The output components 826 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 828 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 818 may include biometric components 839, motion components 834, environmental components 836, or position components 838 among a wide array of other components. For example, the biometric components 839 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 834 may include acceleration sensor components (e.g., accelerometer), gravitation sensor components, rotation sensor components (e.g., gyroscope), and so forth. The environmental components 836 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 838 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 818 may include communication components 840 operable to couple the machine 800 to a network 837 or devices 829 via coupling 824 and coupling 822, respectively. For example, the communication components 840 may include a network interface component or other suitable device to interface with the network 837. In further examples, communication components 840 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 829 may be another machine or any of a wide variety of peripheral devices (e.g., a peripheral device coupled via a USB).

Moreover, the communication components 840 may detect identifiers or include components operable to detect identifiers. For example, the communication components 840 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 840, such as location via Internet Protocol (IP) geo-location, location via Wi-Fi® signal triangulation, location via detecting a NFC beacon signal that may indicate a particular location, and so forth.

Figure 9:
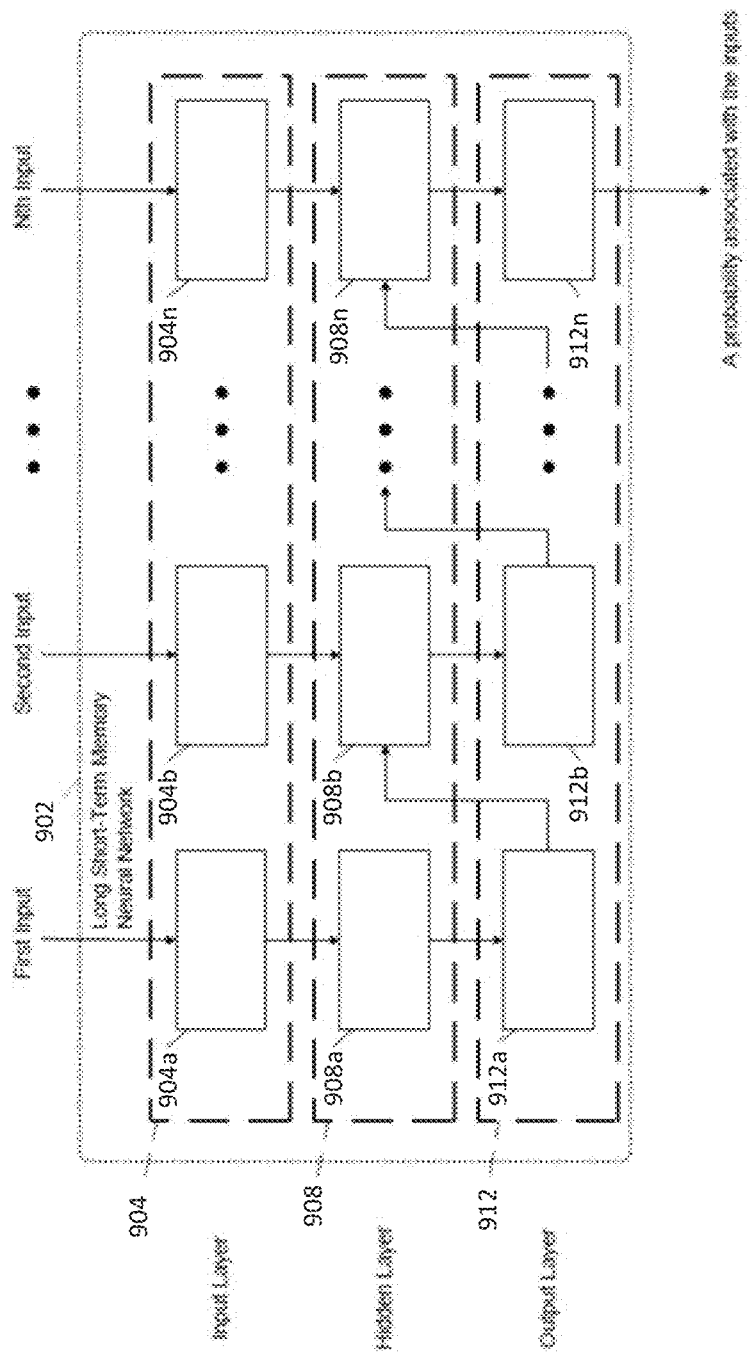
FIG. 9 is a functional block diagram of an example neural network that can be used for the inference engine or other functions (e.g., engines), according to some example embodiments.

FIG. 9 is a functional block diagram of an example neural network 902 that can be used for the inference engine or other functions (e.g., engines) as described herein to produce a predictive model. The predictive model can identify those patients who may benefit from a conversion to a different drug delivery system or methodology relative to the current system. In an example, the neural network 902 can be a LSTM neural network. In an example, the neural network 902 can be a recurrent neural networks (RNN). The example neural network 902 may be used to implement the machine learning as described herein, and various implementations may use other types of machine learning networks. The neural network 902 includes an input layer 904, a hidden layer 908, and an output layer 912. The input layer 904 includes inputs 904a, 904b . . . 904n. The hidden layer 908 includes neurons 908a, 908b . . . 908n. The output layer 912 includes outputs 912a, 912b . . . 912n.

Each neuron of the hidden layer 908 receives an input from the input layer 904 and outputs a value to the corresponding output in the output layer 912. For example, the neuron 908a receives an input from the input 904a and outputs a value to the output 912a. Each neuron, other than the neuron 908a, also receives an output of a previous neuron as an input. For example, the neuron 908b receives inputs from the input 904b and the output 912a. In this way the output of each neuron is fed forward to the next neuron in the hidden layer 908. The last output 912n in the output layer 912 outputs a probability associated with the inputs 904a-904n. Although the input layer 904, the hidden layer 908, and the output layer 912 are depicted as each including three elements, each layer may contain any number of elements. Neurons can include one or more adjustable parameters, weights, rules, criteria, or the like.

In various implementations, each layer of the neural network 902 must include the same number of elements as each of the other layers of the neural network 902. For example, historical patient data may be processed to create the inputs 904a-904n. The output of the neural network 902 may represent a model to produce a score for at least one medication of the plurality of medications. In an example embodiment, the score is indicative of a likelihood of converting the patient from a current dispensing process to an alternate dispensing process. More specifically, the inputs 904a-904n can include prescription related complexity data (binary, vectors, factors or the like) stored in the storage device 110. The prescription related complexity data can be associated with a patient or a grouping of patients. The prescription related complexity data may include medication regiment information for a plurality of medications and patient specific information. The prescription related complexity data may include adherence data relative to the plurality of medications and/or the patient. In an example, an input can be a patient electing to be part of a second delivery mode. In an example, an input can be a patient being prescribed a drug that can be part of the second, different mode of delivery. In an example, an input can be a drug that is part of the second delivery mode. In an example, an input can be whether a patient is a member of a patient group that is eligible to use the second delivery mode. In an example, an input can be a drug that is non-eligible to be part of the second delivery mode. In an example, an input can be a drug that is non-eligible to be part of the second delivery mode when it is paired with a second drug, e.g., these two drugs may not be packaged together. In an example, an input can be a drug that is non-eligible to be part of the multidose delivery mode. The prescription related complexity data can be provided to neurons 908a-908n for analysis and connections between the known facts. The neurons 908a-908n, upon finding connections, provides the potential connections as outputs to the output layer 912, which determines a probability whether the potential connections are from the prescription related complexity data. For example, the neurons 908a-908n can receive multiple prescription related complexity data about a patient.

The neural network 902 can perform any of the above calculations. For example, the neural network 902 can process prescription related complexity data (provided by the inputs 904a-904n) to generate a score for at least one medication of the plurality of medications. The score can be indicative of a likelihood of converting the patient from a current dispensing process to an alternate dispensing process based on any one of or combination of the inputs 904a-904n.

The output of the neural network 902 can be used to trigger a notification associated with converting the patient from the current dispensing process to the alternate dispensing process. For example, the notification can be provided to a PBM, health plan manager, pharmacy, physician, caregiver, and/or any combination thereof to select one or more associated patients or medication regiments for an alternate dispensing methods or for a particular adherence method.

In some embodiments, a convolutional neural network may be implemented. Similar to neural networks, convolutional neural networks include an input layer, a hidden layer, and an output layer. However, in a convolutional neural network, the output layer includes one fewer output than the number of neurons in the hidden layer and each neuron is connected to each output. Additionally, each input in the input layer is connected to each neuron in the hidden layer. In other words, input 904a is connected to each of neurons 908a, 908b . . . 908n.

Glossary

"CARRIER SIGNAL" in this context refers to any intangible medium that is capable of storing, encoding, or carrying transitory or non-transitory instructions for execution by the machine, and includes digital or analog communications signals or other intangible medium to facilitate communication of such instructions. Instructions may be transmitted or received over the network using a transitory or non-transitory transmission medium via a network interface device and using any one of a number of well-known transfer protocols.

"CLIENT DEVICE" in this context refers to any machine that interfaces to a communications network to obtain resources from one or more server systems or other client devices. A client device may be, but is not limited to, a mobile phone, desktop computer, laptop, PDA, smart phone, tablet, ultra-book, netbook, laptop, multi-processor system, microprocessor-based or programmable consumer electronics, game console, set-top box, or any other communication device that a user may use to access a network.

"COMMUNICATIONS NETWORK" in this context refers to one or more portions of a network that may be an ad hoc network, an intranet, an extranet, a virtual private network (VPN), a LAN, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"MACHINE-READABLE MEDIUM" in this context refers to a component, device, or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a stand-alone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"PROCESSOR" in this context refers to any circuit or virtual circuit (a physical circuit emulated by logic executing on an actual processor) that manipulates data values according to control signals (e.g., "commands," "op codes," "machine code," etc.) and which produces corresponding output signals that are applied to operate a machine. A processor may, for example, be a CPU, a RISC processor, a CISC processor, a GPU, a DSP, an ASIC, a RFIC, or any combination thereof. A processor may further be a multi-core processor having two or more independent processors (sometimes referred to as "cores") that may execute instructions contemporaneously.

"TIMESTAMP" in this context refers to a sequence of characters or encoded information identifying when a certain event occurred, for example giving date and time of day, sometimes accurate to a small fraction of a second.

Changes and modifications may be made to the disclosed embodiments without departing from the scope of the present disclosure. These and other changes or modifications are intended to be included within the scope of the present disclosure, as expressed in the following claims.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
receiving, by one or more processors, data associated with a patient, wherein the received data includes medication regiment information for a plurality of medications and patient specific information;
applying a model to the received data to generate a score for at least one medication of the plurality of medications, wherein:
the score is indicative of a likelihood that the patient will successfully convert from a current dispensing process to an alternate dispensing process,
the model includes a machine learning technique having a neural network, and
the machine learning technique is trained to establish a relationship between a plurality of training patient-drug combination features and medication dispensing process conversion likelihoods;
training the machine learning technique by:
obtaining a batch of training data including a first set of the plurality of training patient-drug combination features and medication dispensing process conversion likelihoods;

processing the first set of the plurality of training patient-drug combination features with the machine learning technique to generate estimated medication dispensing process conversion likelihoods;

computing a loss function based on a deviation between the estimated medication dispensing process conversion likelihoods and corresponding medication dispensing process conversion likelihoods of the first set of the plurality of training patient-drug combination features; and updating parameters of the machine learning technique based on the computed loss function; and in response to the generated score exceeding a threshold value, triggering a notification associated with converting the patient from the current dispensing process to the alternate dispensing process.

2. The method of claim 1, further comprising:

in response to receiving a confirmation to the notification, converting from the current dispensing process to the alternate dispensing process, wherein:

the current dispensing process includes dispensing each of the plurality of medications individually, and the alternate dispensing process includes dispensing two or more medications of the plurality of medications in a multiple-dose package; and providing a next dosage of medication to the patient via the alternate dispensing process.

3. The method of claim 2, wherein the multiple-dose package includes a single package that has multiple doses of different medications including the two or more medications.

4. The method of claim 2, wherein the multiple-dose package includes one or more pouches organized by a prescribed day and time of dose of each of the two or more medications.

5. The method of claim 1, further comprising:

identifying a medication that is incompatible with a multiple-dose package; and in response to identifying the medication that is incompatible with the multiple-dose package, selecting as the alternate dispensing process one or more of:

providing automatic dose and refill reminders, providing automatic refill and renewal for the plurality of medications, synchronizing medication, identifying lower cost alternatives, providing home delivery of the plurality of medications, and providing one or more adherence aids.

6. The method of claim 1, wherein:

triggering the notification includes providing a message to an operator of a pharmacy benefit manager, the message identifies the patient and the score associated with the at least one medication of the plurality of medications, and the operator performs an outreach event to communicate with the patient to modify the current dispensing process.

7. The method of claim 1, wherein triggering the notification includes providing a message to the patient with an option to automatically modify the current dispensing process.

8. The method of claim 1, wherein:

the model computes the score based on one or more criteria, and the one or more criteria includes medication data that specifies medications that are incompatible with the alternate dispensing process and that specifies medication mixing exclusion information.

9. The method of claim 1, wherein the model computes the score based on one or more criteria including at least one of: profitability information indicative of a level of profitability from converting the patient from the current dispensing process to the alternate dispensing process, quantity of pharmacies used to obtain the plurality of medications, quantity of prescribing physicians of the plurality of medications, history of adherence to the plurality of medications, or patient demographic information.

10. The method of claim 1, wherein:

the score is a first score, the at least one medication is a first medication, and the method further includes:

applying the model to the received data to generate a second score for a second medication of the plurality of medications, wherein the second score is indicative of a likelihood of converting the patient from the current dispensing process to the alternate dispensing process for the second medication; and ranking the first and second medications based on the first and second scores.

11. The method of claim 10, further comprising:

selecting the second medication for converting the patient from the current dispensing process to the alternate dispensing process based on the ranking;

identifying a third medication that is compatible with the alternate dispensing process of the second medication; and generating the notification based on a combination of the second and third medications.

12. The method of claim 1, wherein:

the patient-drug combination features include medication and demographic information for a plurality of patients, and the medication dispensing process conversion likelihoods indicate whether each of the plurality of patients converted from the current dispensing process to the alternate dispensing process for the respective medications.

13. The method of claim 1, further comprising:

generating, for each of the plurality of medications, patient-drug combination features based on the received data; and applying the machine learning technique to the patient-drug combination features to generate a plurality of scores for each of the plurality of medications.

14. A system comprising:

one or more processors coupled to a non-transitory computer-readable medium having computer instructions that when executed by the one or more processors perform operations including:

receiving data associated with a patient, wherein the received data includes medication regiment information for a plurality of medications and patient specific information;

applying a model to the received data to generate a score for at least one medication of the plurality of medications, wherein:

the score is indicative of a likelihood that the patient will successfully convert from a current dispensing process to an alternate dispensing process, the model includes a machine learning technique having a neural network, and the machine learning technique is trained to establish a relationship between a plurality of training patient-drug combination features and medication dispensing process conversion likelihoods;
training the machine learning technique by:
obtaining a batch of training data including a first set of the plurality of training patient-drug combination features and medication dispensing process conversion likelihoods;
processing the first set of the plurality of training patient-drug combination features with the machine learning technique to generate estimated medication dispensing process conversion likelihoods;
computing a loss function based on a deviation between the estimated medication dispensing process conversion likelihoods and corresponding medication dispensing process conversion likelihoods of the first set of the plurality of training patient-drug combination features; and
updating parameters of the machine learning technique based on the computed loss function; and
in response to the generated score exceeding a threshold value, triggering a notification associated with converting the patient from the current dispensing process to the alternate dispensing process.

15. The system of claim 14, further comprising:
in response to receiving a confirmation to the notification, converting from the current dispensing process to the alternate dispensing process, wherein:
the current dispensing process includes dispensing each of the plurality of medications individually, and
the alternate dispensing process includes dispensing two or more medications of the plurality of medications in a multiple-dose package; and
providing a next dosage of medication to the patient via the alternate dispensing process.

16. The system of claim 15, wherein the multiple-dose package includes a single package that has multiple doses of different medications including the two or more medications.

17. The system of claim 15, wherein the multiple-dose package includes one or more pouches organized by a prescribed day and time of dose of each of the two or more medications.

18. A non-transitory computer-readable medium comprising instructions including:
receiving data associated with a patient, wherein the received data includes medication regiment information for a plurality of medications and patient specific information;
applying a model to the received data to generate a score for at least one medication of the plurality of medications, wherein:
the score is indicative of a likelihood that the patient will successfully convert from a current dispensing process to an alternate dispensing process,
the model includes a machine learning technique having a neural network, and
the machine learning technique is trained to establish a relationship between a plurality of training patient-drug combination features and medication dispensing process conversion likelihoods;
training the machine learning technique by:
obtaining a batch of training data including a first set of the plurality of training patient-drug combination features and medication dispensing process conversion likelihoods;
processing the first set of the plurality of training patient-drug combination features with the machine learning technique to generate estimated medication dispensing process conversion likelihoods;
computing a loss function based on a deviation between the estimated medication dispensing process conversion likelihoods and corresponding medication dispensing process conversion likelihoods of the first set of the plurality of training patient-drug combination features; and
updating parameters of the machine learning technique based on the computed loss function; and
in response to the generated score exceeding a threshold value, triggering a notification associated with converting the patient from the current dispensing process to the alternate dispensing process.

* * * * *